United States Patent [19]

Kisielewski et al.

[11] Patent Number: 5,658,146
[45] Date of Patent: Aug. 19, 1997

[54] DENTAL IMPLANT

[75] Inventors: Richard W. Kisielewski, Columbia, Md.; Cheryl K. Hastings, Warsaw, Ind.; George R. McCarthy, Potomac, Md.

[73] Assignee: The United States of America as represented by the Secretary of the Department of Health and Human Services, Washington, D.C.

[21] Appl. No.: 424,786

[22] Filed: Apr. 19, 1995

[51] Int. Cl.⁶ .......................... A61C 13/12; A61C 13/225
[52] U.S. Cl. .......................................................... 433/172
[58] Field of Search .................................. 433/172, 173, 433/174, 175, 176, 169

[56] References Cited

U.S. PATENT DOCUMENTS

| | | | |
|---|---|---|---|
| 3,435,526 | 4/1969 | Brancato. | |
| 4,016,651 | 4/1977 | Kawahara et al.. | |
| 4,746,293 | 5/1988 | Lundgren et al.. | |
| 4,756,689 | 7/1988 | Lundgren et al. | 433/169 |
| 5,006,069 | 4/1991 | Lazzara et al. | 433/173 |
| 5,015,186 | 5/1991 | Detsch | 433/173 |
| 5,110,292 | 5/1992 | Balfour et al.. | |
| 5,116,225 | 5/1992 | Riera | 433/173 |

FOREIGN PATENT DOCUMENTS 2611464  2/1987  France.

*Primary Examiner*—Cary E. O'Connor
*Attorney, Agent, or Firm*—Townsend and Townsend and Crew

[57] ABSTRACT

A device for securing a dental prothesis to a base implanted into body tissue of a patient has a stud which is secured to the base and has a cylindrical body and a threaded free end. A tubular spacer surrounds the stud, is supported on the base, and terminates short of the free stud end. A tubular cup is supported on the spacer and has a through hole defining a first hole section of a first diameter about equal to an inner diameter of the tubular spacer and a second hole section of a diameter larger than the inner diameter of the tubular spacer. An annular ledge is positioned between the first and second hole sections, extends radially inwardly to proximate the threaded free end of the stud, and defines a bearing surface facing away from the tubular space. A retaining nut is threaded onto the threaded free end of the stud and has an under side in engagement with the bearing surface which, upon tightening of the nut on the stud, firmly presses the cup against the tubular spacer. The nut can be turned relative to the stud to increase the force with which the cup and the spacer are pressed against the base. The nut and the bearing surface and/or the threaded free end of the stud are constructed to inhibit relative rotation of the nut, and a resulting loosening of the dental prosthesis on the base, by increasing friction between them.

27 Claims, 1 Drawing Sheet

DENTAL IMPLANT

BACKGROUND OF THE INVENTION

The present invention relates to dental implants of the type in which a base is initially implanted in a patient's jaw where it is left for a period of time to permit bony ingrowth into the surface of the base to permanently affix it in the bone so that the base effectively forms a unit with the surrounding bone. Thereafter, a spacer; for example, made of titanium, is secured to the base and a dental prosthesis; for example, in the form of a crown or a bridge, is anchored to the base. A so-called cup, which may be an integral part of a bridge, for example, rests on top of the spacer and is secured with a retaining screw or nut.

While space is severely limited, dental prostheses are subjected to large forces acting in different directions which can put severe strain on the implant structure. The problem is particularly severe because in a space smaller than the cross-section of the tooth a tubular spacer must be located which transfers the forces to which the implant is subjected to the base implanted in the bone. The spacer must be configured so that there is room for anchoring the prosthesis with a screw and/or nut.

While screw and/or nut connections are very useful to assemble and install prostheses, any relative rotation thereof can lead to a highly undesirable loosening of the implant, which, if permitted to occur, requires under the best of circumstances an immediate visit to a dentist, but which can also lead to damage or the destruction of the implant and/or surrounding body tissue.

Some implants of this type employ a spacer screw which is concentrically disposed inside the tubular spacer and which has one end threaded into the base anchored in the bone. The other end of the spacer screw has a threaded hole which receives a retaining screw that engages the earlier-mentioned cup and presses it against the tubular spacer and hence the implanted base to secure the cup and therewith the dental prosthesis to the base.

Since the implant components, and in particular the base, the spacer screw, the cup and the attachment screw or bolt, are stacked, the thread sizes decrease over the height of the stack so that the diameter of the retaining screw thread can be no more than about two-thirds the diameter of the spacer screw thread engaging the base. Moreover, the retaining screw head is similarly small so that frictional forces which hold the retaining screw in place after it has been tightened are relatively small. The large, multidirectional forces to which the implant is subjected can lead to a loosening of the retaining screw, which in turn results in a highly undesirable and potentially damaging loosening of the dental prosthesis.

U.S. Pat. No. 4,746,293 discloses an improved variant of such a dental implant in which, instead of a separate retaining screw, the spacer screw includes a threaded stud at its free end which projects into the cup and which is engaged by a nut which, upon tightening, presses the cup against the spacer and the implanted base to thereby secure the dental prosthesis to the base. In the arrangement disclosed in that patent, the threaded stud on the spacer screw can have a relatively larger diameter than the earlier-discussed threaded holes, which enhances friction between the stud and the nut and thereby makes a loosening of the nut less likely.

However, in the arrangement disclosed in that patent, space for the nut is limited and it engages the cup along a narrow annular bearing surface the outermost diameter of which is less than an inner diameter of the tubular spacer. This narrow annular bearing surface contributes little to frictionally securing the nut against rotation. Further, the dental prosthesis disclosed in that patent is constructed to permit limited relative pivotal movements between the cup and the tubular spacer. Giving the nut an outer diameter less than the inner diameter of the tubular spacer and interposing an O-ring between them facilitates such relative pivotal motions.

A drawback of this arrangement is that the axial holding forces generated by the nut cannot be transferred to the tubular spacer in an axial direction, which can lead to the generation of undesirable force components between the cup and the spacer. Another drawback of this arrangement is that the frictional forces generated between the components of the implant are relatively small and, therefore, do not efficiently prevent turning of the nut and the resulting loosening of the implant.

Accordingly, there is presently a need for a dental implant which is effective in securing the dental prosthesis to the implanted base and prevents relative rotation of the implant components, and particularly of the retaining nut or screw and a resulting loosening of the prosthesis.

SUMMARY OF THE INVENTION

The present invention improves dental implants by preventing, or at least greatly inhibiting, the undesirable loosening of the dental prosthesis due to a turning of the retaining screw or nut which secures the prosthesis to the base implanted in a patient's bone (e.g. jaw) and by further providing for a linear, axial transmission of forces from the prosthesis to the tubular spacer and the implanted base by securing the cup of the prosthesis with a retaining nut which is sufficiently enlarged so that the nut extends over the axial projection of the tubular sleeve. An advantage of the present invention is that it permits a retrofitting of existing dental prostheses by substituting the enlarged retaining nut for the relatively small-diameter retaining nuts or screws which were heretofore used and which were prone to failure due to loosening when the nut or screw turned under the forces encountered during use.

Generally speaking, this is achieved by providing an anchoring system for the dental prosthesis including a spacer screw, one end of which is threaded into the implanted base and the other, free end of which is threaded. A tubular spacer surrounds the spacer screw, has one end supported on the base, and has another end proximate the free, threaded end of the spacer screw. A tubular cup has a through hole and a first end supported on the tubular spacer, a second free end, and an inwardly protruding ledge located intermediate the ends of the cup. A first portion of the through hole in the cup between the ledge and the first end of the cup is sized to accommodate the spacer screw and a diameter which preferably is about equal to the inner diameter of the tubular spacer. A second portion of the through hole on the other side of the ledge has a sufficiently larger diameter to enable use of a retaining nut with an outer diameter larger than the inner diameter of the tubular spacer. When threaded onto the free end of the spacer screw, an under side of the nut engages the ledge and, upon tightening of the nut, firmly secures the cup and therewith the tubular spacer to the implanted base.

As a result of the above-summarized construction, forces generated by the retaining nut upon its tightening are transmitted axially from the cup directly to the tubular spacer because the under side of the nut, which transmits the tightening forces to the cup, overlies or is axially aligned with the wall of the tubular spacer.

The relatively larger diameter of the free, threaded end of the spacer screw and the relatively large annular surface of the under side of the retaining nut significantly increase friction between the nut, the spacer screw and the cup. This in and of itself reduces the likelihood that the nut might turn under forces applied encountered during use of the dental prosthesis.

To further and more positively inhibit undesirable turning of the retaining nut, another aspect of the present invention places a ring constructed of a relatively high friction material, such as polyoxymethylene, in a ring groove formed in the under side of the nut so that the high friction ring engages the radially inwardly projecting ledge of the cup, and preferably also the threaded free end of the spacer screw, thereby greatly increasing friction between the nut and the ledge.

Alternatively and/or additionally, friction is further increased, and unintended turning of the nut is prevented or at least further inhibited, by forming a plurality of slits in the end of the nut facing away from the ledge, or castellating the nut, to form a plurality of circumferentially spaced nut segments an inside of which is threaded and engages the threaded free end of the spacer screw. The sectors can be slightly deformed so that they are resiliently biased against the free threaded end of the spacer screw, and/or the thread on the inside of the segments can be tapered, thereby significantly enhancing the friction between the nut and the spacer screw over what is possible when utilizing conventional nuts. This further inhibits undesirable rotation of the nut.

Optimally, at least an upper end of the nut is given a round cross-section, as is common for castellated nuts, and a cap with an annular skirt is placed over the nut. The skirt is dimensioned so that it applies an inwardly directed biasing force to the nut segments to increase the force with which the segments are pressed against the thread of the spacer screw. Additional friction is thereby generated between them. Preferably, the cap is threaded onto the free end of the spacer screw, and the interface between the skirt and the upper end of the nut is angularly inclined with respect to the axis of the nut so that a tightening of the nut gradually increases the force with which the nut segments are biased against the spacer screw.

If desired, the cap can be constructed with a closed transverse member so that it completely encapsulates and thereby seals the threaded end of the spacer nut to prevent liquids and/or contaminants from entering, by forming a blind threaded hole in the cup.

An additional advantage attained with the present invention is that the above-summarized construction of the improved dental prosthesis lends itself ideally for retrofitting prostheses constructed in accordance with the prior art; e.g. prostheses which utilize small-diameter retaining screws or nuts for securing the cup and the tubular spacer to the base. Retrofitting is accomplished by removing the previously installed prosthesis from the base, and enlarging a portion of the through hole in the cup between the inwardly projecting ledge and the upper end of the nut to a diameter larger than the inner diameter of the tubular spacer and sufficiently large to receive therein a retaining nut with an outer diameter that is larger than the inner diameter of the tubular spacer. If necessary; that is, if the existing prosthesis was secured to the spacer screw with a retaining screw extending into a threaded hole in the free end of the former, an adapter is initially threaded into the hole. The adapter is secured; e.g. bonded, to the spacer screw and includes a threaded stud which projects into the cup and past the ledge thereof a sufficient distance to receive the retaining nut and, if used, the cap for biasing the segments of the castellated nut with greater force against the threaded spacer screw.

DESCRIPTION OF THE PREFERRED EMBODIMENTS

Figure 2:
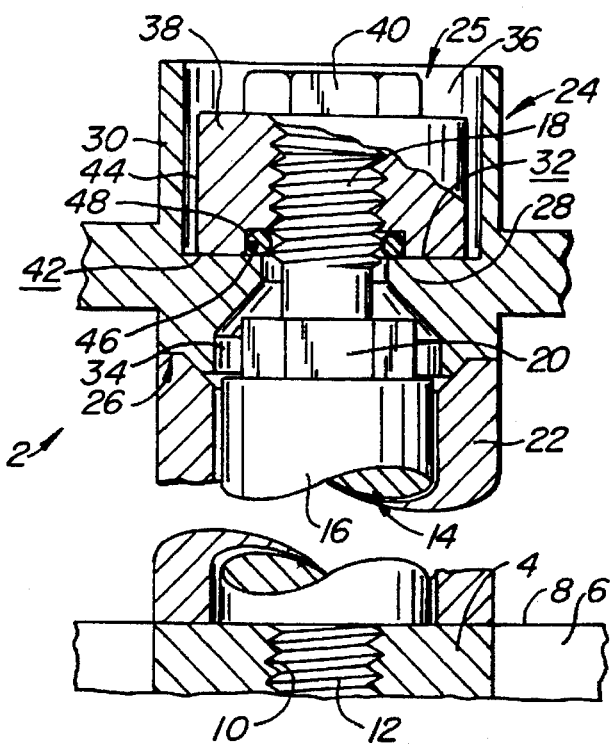
FIG. 2 is a fragmentary illustration of a dental prosthesis constructed in accordance with the present invention.

Referring first to FIG. 2, a dental implant 2 constructed in accordance with the present invention includes a base 4 which is implanted into live jaw tissue 6 of a patient. The base ends at about a gum line 8 and includes a threaded hole 10 which receives a threaded end 12 of a spacer screw 14. The spacer screw includes an enlarged-diameter, cylindrical center portion 16 and terminates in an upwardly extending threaded free end or stud 18. A square, hexagonal or other appropriately shaped projection between the cylindrical center portion and the free threaded end of the spacer screw is provided for gripping the screw with a tool, such as a wrench (not shown), and tightening it onto base 4.

A tubular spacer 22 surrounds the cylindrical portion 16 of the spacer screw and has an inner diameter only slightly larger than the diameter of the cylindrical center portion so that it can be slipped thereover. The lower end of the spacer rests on and is supported by the upwardly facing surface of base 4. A generally tubular cup 24, which is part of the prosthesis, has a first, lower end 26 which rests on and is supported by the upper end of the tubular sleeve, a through bore 25, and an annular projection or ledge 28 which extends radially inwardly from a wall 30 of the cup. The projection defines an upwardly facing bearing surface 32, divides the through bore into first and second, lower and upper, respectively, hole sections 34, 36, and forms a constriction in the through bore which is spaced from the respective ends of the latter.

The lower hole section 34 has a diameter about equal to the inner diameter of tubular spacer 22 and a sufficient length to accommodate the hexagonal projection 20 between the cylindrical portion 16 and stud 18 of the spacer screw by appropriately positioning ledge 28.

The upper hole section 36 of cup 24 has a larger diameter than the lower hole section 34, and therefore also a larger diameter than the inside diameter of the tubular spacer, so that it can receive a retaining nut 38. The retaining nut has a preferably cylindrical periphery 44 of a diameter larger than the inside diameter of spacer 22 and is threaded onto stud 18. A hexagonal, or other appropriately shaped extension 40 on top of the retaining nut is provided so that it can be tightened onto stud 18 with an appropriate tool such as a wrench (not shown).

As can be seen in FIG. 2, upon the tightening of retaining nut 38 its under side 42 engages bearing surface 32 of the ledge, presses cup 24 and tubular spacer 22 against the upwardly oriented face of base 4, and thereby firmly secures the prosthesis to the base and hence the bone tissue. Since the periphery 44 of the nut overlies the axial projection of the tubular wall of spacer 22, the axially oriented forces generated by the tightened nut are transmitted directly; that is, axially, and not at an oblique angle, from the nut past the lower portion of cup 24 to the upper end of the spacer and from there to base 4. This prevents the generation of nonaxial force components which might adversely affect the interengagement of the nut, cup, spacer and base.

Figure 3:
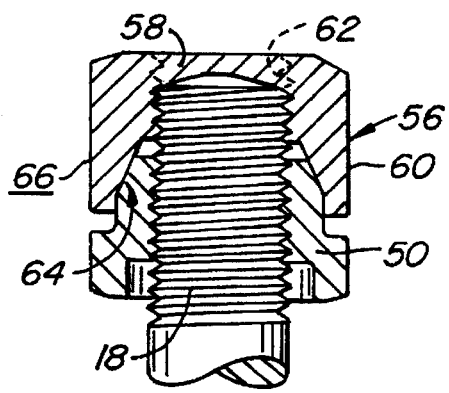
FIG. 3 is a partial elevational view, in section, illustrating the high friction connection between the threaded free end of the spacer screw and a retaining nut including a friction-enhancing cap cooperating with the nut.
Figure 4:
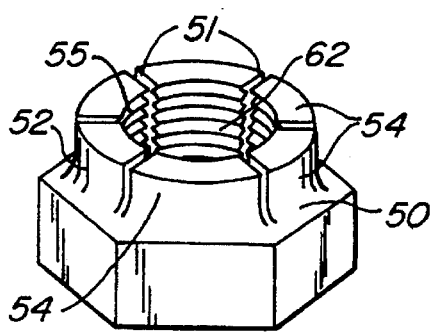
FIG. 4 is a perspective view of a castellated nut utilized in the arrangement shown in FIG. 3.

Referring now to FIGS. 2–4, to enhance friction and thereby more positively prevent or at least inhibit rotation of nut 38 on stud 18, and a resulting loosening of the dental prosthesis 2, a ring groove 46 is formed in the under side 42 of the nut. Preferably, the ring groove is open in a radially inward direction and a ring 48 constructed of a relatively high friction material such as polyoxymethylene is disposed in the groove. The ring is dimensioned so that, upon a tightening of the nut, the ring is compressed. The ring groove is radially inwardly open so that the compression of the ring results in frictional engagement between the ring and both the bearing surface 32 of ledge 28 and the threads of stud 18. This generates frictional forces between the nut, the bearing surface, and the stud, which increases the torque required for turning the nut and thereby inhibits or prevents its unintended loosening during use.

Alternatively or additionally, the nut is a castellated nut 50 at least an upper portion 52 of which has an outer periphery which, in cross-section, is circular and includes a plurality of, say, six axially oriented slit 51 which extend from an upper end of the nut towards about its midportion and define a plurality of nut segments 54.

An inside 55 of the nut segments is threaded to engage stud 18. In one preferred embodiment the thread is tapered in an axial direction to more firmly grip the stud. Alternatively, the nut segments can be given a slight inward bias so that, when the nut is threaded onto stud 18, the stud resiliently deflects the segments outwardly. Both alternatives generate a radially acting force between the threads on the segments and the stud which increases friction and thereby inhibits unintentional turning of the nut on the stud.

Preferably a cap 56, molded from a plastic material such as polyoxymethylene, for example, has a generally disc-shaped body 58 from which a skirt 60 extends in an axial, downward (as seen in FIG. 3) direction. In one embodiment the cap has a through hole 62 (partially shown in broken lines in FIG. 3) which is threaded so that the cap can be screwed onto stud 18. In an alternative embodiment, the threaded hole is a blind hole and the disc-shaped body 58 of the cap forms a closure over the end of stud 18 as is shown in FIG. 3.

When castellated nut 50 is used in conjunction with cap 56, the cooperating surfaces of the nut and the cap converge angularly in a direction away from base 4 (shown in FIG. 2) to define a frustoconical interface 64 between them. This permits the cap to be turned relative to the nut to increase or decrease the radially inwardly directed force component generated along the interface to thereby correspondingly adjust the friction generated between the nut segments 54 and stud 18 to inhibit or prevent subsequent unintended turning of the retaining nut during use of the prosthesis. To facilitate turning of the cap on the stud, provisions are made for turning the cap on the stud with an appropriate tool by, for example, giving the periphery 66 of the cap a hexagonal shape.

In use, the castellated nut 50 is typically threaded onto stud 18 and tightened to the needed torque to apply the desired holding force to cup 24 and tubular spacer 22. Thereafter cap 56 is threaded onto the free end of the stud and torqued so that nut segments 54 are forced inwardly against the stud with the force necessary to generate the desired additional friction between the retaining nut and the stud to inhibit or prevent rotation of the nut. When threaded hole 62 in the cap is a blind hole, the cap completely covers and seals the stud.

Figure 1:
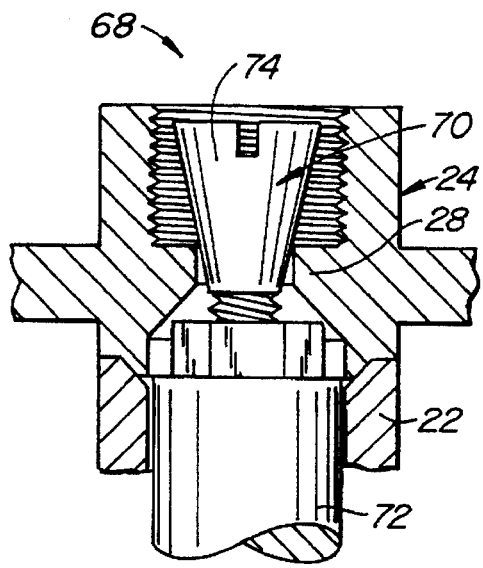
FIG. 1 is a fragmentary illustration of a dental prosthesis constructed in accordance with the prior art.
Figure 5:
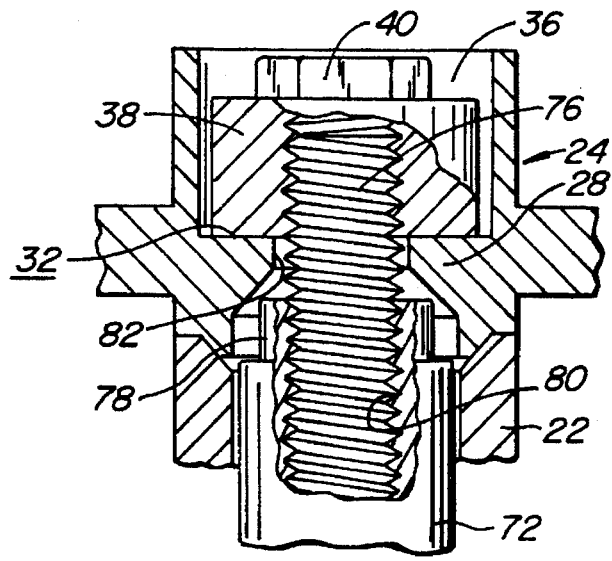
FIG. 5 is a view similar to FIG. 2 and illustrates the retrofitting of an existing dental prosthesis as shown in FIG. 1 to convert the latter into a dental prosthesis constructed in accordance with the present invention.

Referring to FIGS. 1 and 5, the present invention also enables a retrofitting of dental prostheses 68 (shown in FIG. 1) constructed in accordance with the prior art and having, for example, a retaining screw 70 threaded into a threaded bore (not shown) in the upper free end of a spacer screw 72. The head 74 of the retaining screw engages the ledge 28 of a cup 24 in the manner shown in FIG. 1 to secure the cup to a tubular spacer 22 and the implanted base (shown in FIGS. 1 and 5).

The prior art implant shown in FIG. 1 is converted in accordance with the present invention into the dental prosthesis of the present invention by first removing retaining screw 70 and cup 24 from the base. Thereafter a threaded retrofit stud 76, which preferably has the same diameter as threaded end 12 (shown in FIG. 2) of existing spacer screw 72, is attached to the latter; for example, by replacing hex nut 78 at the upper end of the spacer screw if, on the existing screw, the nut was separately attached thereto. Alternatively, the free end of the spacer screw can be bored out and rethreaded, or an existing threaded bore 80 can be enlarged and rethreaded so that it can threadably receive the retrofit stud 76.

Bore 82 formed by ledge 28 of the previously removed cup 24 is enlarged so that it can pass over threaded stud 76. The upper hole section 36 of cup 24 is also enlarged to accept the previously described retaining nut 38.

Thereafter cup 24 is placed over stud 76 and secured to tubular spacer 22 and base 4 (shown in FIG. 2, not shown in FIGS. 1 and 5) by tightening retaining nut 38 in the above-described manner. Existing dental prostheses, which have the earlier-discussed shortcomings, can be retrofitted in this manner to attain the advantages of the present invention without, however, requiring an entirely new prosthesis. Retrofitting can thereby be effected at costs significantly less than what it would cost to fit the patient with a new dental prosthesis.

Of course, a high friction generating nut, such as the castellated nut and nut assembly shown in FIGS. 3 and 4, can be substituted for nut 38 shown in FIG. 5 to effect desired increases in the frictional holding force for the nut.

What is claimed is:

1. Apparatus for connecting a dental prosthesis to an anchoring system for the prosthesis including a stud with a cylindrical center portion having a first end threaded into a base implanted into live tissue of a patient and a second threaded end extending away from the cylindrical center portion, and a tubular spacer surrounding the cylindrical center portion and extending from the base to an end proximate the threaded end of the stud, the apparatus comprising a tubular cup with a through hole having a first end adapted to rest on the tubular spacer and a second end remote therefrom, a ledge disposed between the ends of the cup and protruding into the through hole, a first portion of the through hole between the ledge and the first end having a diameter to accommodate the stud and a second portion of the through hole between the ledge and the second end of the cup having a diameter which is larger than an inner diameter of the spacer; and a nut disposed in the second portion of the through hole for threadably engaging the threaded end of the stud, the nut having a periphery which is larger thorn the inner diameter of the tubular spacer, at least portions of a surface of the ledge and of the nut which are in engagement with each other being in axial alignment with at least portions of surfaces of the cup and the tubular spacer which are in engagement with each other so that forces generated when the nut is tightened onto the threaded end of the stud are transmitted from the nut to the tubular spacer in substantially an axial direction only.

2. Apparatus according to claim 1 wherein the ledge is a continuous, ring-shaped ledge.

3. Apparatus according to claim 1 wherein the nut has a cylindrical periphery.

4. Apparatus according to claim 1 including an annular insert at an end of the cup engaging the ledge, the insert being constructed of a material which increases friction between the nut and the ledge to inhibit relative rotation of the nut.

5. Apparatus according to claim 4 wherein the insert is a ring constructed of a plastic material.

6. Apparatus according to claim 5 wherein the insert comprises a ring constructed of polyoxymethylene.

7. Apparatus for connecting a dental prosthesis to an anchoring system for the prosthesis including a stud with a cylindrical center portion having a first end threaded into a base implanted into live tissue of a patient and a second threaded end extending away from the cylindrical center portion, and a tubular spacer surrounding the cylindrical center portion and extending from the base to an end proximate the threaded end of the stud, the apparatus comprising a tubular cup with a through hole having a first end adapted to rest on the tubular spacer and a second end remote therefrom, a ledge disposed between the ends of the cup and protruding into the through hole, a first portion of the through hole between the ledge and the first end having a diameter to accommodate the stud and a second portion of the through hole between the ledge and the second end of the cup having a diameter which is larger than an inner diameter of the spacer; a nut disposed in the second portion of the through hole for threadably engaging the threaded end of the stud, the nut having a periphery which is larger than the inner diameter of the tubular spacer, wherein a portion of the nut seated on the ledge is cylindrical; and a member projecting from an end of the nut facing away from the ledge which is adapted to be engaged by a nut turning instrument.

8. Apparatus according to claim 7 wherein the member for turning the nut comprises a hexagonal projection.

9. Apparatus for connecting a dental prosthesis to an anchoring system for the prosthesis including a stud with a cylindrical center portion having a first end threaded into a base implanted into live tissue of a patient and a second threaded end extending away from the cylindrical center portion, and a tubular spacer surrounding the cylindrical center portion and extending from the base to an and proximate the threaded end of the stud, the apparatus comprising a tubular cup with a through hole having a first end adapted to rest on the tubular spacer and a second end remote therefrom, a ledge disposed between the ends of the cup and protruding into the through hole, a first portion of the through hole between the ledge and the first end having a diameter to accommodate the stud and a second portion of the through hole between the ledge and the second end of the cup having a diameter which is larger than an inner diameter of the spacer; a nut disposed in the second portion of the through hole for threadably engaging the threaded end of the stud, the nut having a periphery which is larger than the inner diameter of the tubular spacer, wherein an end of the nut facing away from the ledge is slitted to define a plurality of relatively flexible nut segments, the segments carrying a thread on interior sides thereof for engaging the threaded stud end; and means for enhancing friction between the interior sides of the segments and the threaded stud end to thereby inhibit relative rotation between them.

10. Apparatus according to claim 9 wherein the friction enhancing means is defined by an inward bias of the segments towards the threaded stud end.

11. Apparatus according to claim 9 wherein the friction enhancing means is defined by a tapered thread on the interior sides of the segments.

12. Apparatus according to claim 9 wherein the end of the nut has a circular periphery.

13. Apparatus according to claim 12 wherein the friction enhancing means includes a cap threaded onto the threaded stud end comprising a skirt forming an internal surface surrounding and in engagement with the end of the nut for maintaining the segments in tight engagement with the threaded stud end.

14. Apparatus according to claim 13 wherein the end of the nut and the skirt define generally conical surfaces in engagement with each other and which converge in the direction of the second end of the cup so that upon relative rotation of the cap with respect to the nut a force with which the cap biases the nut segments towards the threaded stud end can be varied for adjusting the friction between the threaded stud end and the segments.

15. Apparatus according to claim 14 wherein an exterior, axially extending surface of the cap is defined by a plurality of opposing, flat surfaces for turning the gap on the threaded stud end.

16. Apparatus for securing a dental prothesis to a base implanted into body tissue of a patient comprising:

a stud adapted to be secured to the base having a cylindrical body and a threaded free end;

a tubular spacer surrounding the stud, adapted to be supported on the base and terminating short of the free end;

a tubular cup having a first end supported on the spacer and a second end spaced therefrom, the cup defining a through hole forming a first hole section of a first diameter about equal to an inner diameter of the tubular spacer and terminating at the first end and a second hole section of a diameter larger than the inner diameter of the tubular spacer and terminating at the second end, and an annular ledge positioned between the first and second hole sections and extending radially inwardly to proximate the threaded free end to define a bearing surface facing the second end of the cup; and a nut threaded onto the threaded free end having an under side in engagement with the bearing surface which, upon tightening of the nut on the threaded free end, firmly presses the cup against the tubular spacer, the nut including means accessible through the second end of the cup for turning the nut relative to the stud and means for enhancing friction between the nut and at least one of the bearing surface and the threaded free end to inhibit relative rotation of the nut and a resulting loosening of the dental prosthesis on the base.

17. Apparatus according to claim 16 wherein the friction enhancing means comprises a member disposed between at least a portion of the bearing surface and a portion of the under side of the nut for increasing friction between the nut and the cup.

18. Apparatus according to claim 17 wherein the member comprises a ring disposed in an open groove in the under side of the nut.

19. Apparatus according to claim 18 wherein the ring is constructed of polyoxymethylene.

20. Apparatus according to claim 16 wherein the friction enhancing means comprises slits extending in an axial direction from an end of the nut opposite the under side thereof to define circumferentially spaced nut segments, the segments being biased radially inwardly to increase friction between the nut and the threaded free end.

21. Apparatus according to claim 16 wherein the friction enhancing means comprises slits extending in an axial direction from an end of the nut opposite the under side thereof to define circumferentially spaced nut segments, an inside of the segments carrying a tapered thread engaging the threaded free end and generating increased friction between the segments and the threaded free end.

22. Apparatus according to claim 16 wherein the friction enhancing means includes a member encircling the segments and biasing the segments radially inwardly to increase friction between the nut and the threaded free end.

23. Apparatus according to claim 22 wherein the member threadably engages the threaded free end.

24. Apparatus according to claim 23 wherein the member and the nut define cooperating, conically shaped surfaces so that, upon rotation of the member relative to the nut, a force biasing the sectors radially inwardly can be varied.

25. Apparatus according to claim 23 wherein the member includes a threaded blind hole engaging the threaded end.

26. A method for retrofitting a connection between a dental prosthesis and an existing anchoring system for the prosthesis, the system including a base implanted in body tissue of a patient, and a spacer screw projecting away from the base and having a free end including an axially oriented threaded hole and a threaded retaining screw engaging the hole and securing the prosthesis to the spacer screw, the prosthesis including a cup having an internal through hole with a radially inwardly protruding constriction spaced from respective first and second ends of the cup and engaged by the retaining screw for securing the prothesis to the base, the method comprising the steps of removing the retaining screw and the cup from the spacer screw; enlarging a portion of the through hole in the cup between the constriction and the second end of the cup to a diameter larger than an inner diameter of the tubular spacer; non-rotatably securing a threaded stud to the spacer screw so that the threaded stud projects axially past the constriction into the enlarged diameter portion of the through hole; providing a retaining nut adapted to be threaded onto the threaded stud and having an outer diameter which is larger than the inner diameter of the tubular spacer; and with the retaining nut securing the cup to the threaded stud and therewith to the tubular spacer and the base by tightening the nut against the constriction in the cup.

27. Apparatus for connecting a dental prosthesis to an anchoring system for the prosthesis including a stud with a cylindrical center portion, a first end threaded into a base implanted into live tissue of a patient and a second threaded end extending away from the cylindrical center portion, and a tubular spacer surrounding the cylindrical center portion and extending from the base to an end face proximate the threaded end of the stud which faces away from the base, the apparatus comprising a tubular cup with a through hole having a first end adapted to rest on the end face of the tubular spacer and a second end remote therefrom, a ledge disposed between the ends of the cup defining a first bearing surface oriented towards the second end and protruding into the through hole, a first portion of the through hole between the ledge and the first end having a diameter to accommodate the stud and a second portion of the through hole between the ledge and the second end of the cup having a diameter which is larger than an inner diameter of the spacer so that at least a portion of the first bearing surface overlies the end face of the spacer; and a nut disposed in the second portion of the through hole for threadably engaging the threaded end of the stud, the nut having a second bearing surface of a diameter which is larger than the inner diameter of the tubular spacer for engaging the first bearing surface so that forces generated when the nut is tightened onto the threaded end of the stud are transmitted from the nut via the first and second bearing surfaces and the end face of the spacer to the base in substantially only an axial direction.

\* \* \* \* \*